(12) United States Patent
Cavaillon et al.

(10) Patent No.: US 7,521,042 B2
(45) Date of Patent: Apr. 21, 2009

(54) PHARMACEUTICAL AEROSOL FORMULATION

(75) Inventors: Pascal Cavaillon, Evreux Cedex (FR);
Nathalie Llorca, Evreux Cedex (FR);
Olivier Louis, Evreux Cedex (FR);
Patrick Rosier, Evreux Cedex (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 1078 days.

(21) Appl. No.: 10/364,257

(22) Filed: Feb. 11, 2003

(65) Prior Publication Data

US 2003/0157032 A1    Aug. 21, 2003

Related U.S. Application Data

(63) Continuation of application No. 09/673,426, filed as application No. PCT/EP99/02535 on Apr. 15, 1999, now abandoned.

(30) Foreign Application Priority Data

Apr. 18, 1998    (GB)    ................... 9808152.4
Jul. 8, 1998    (GB)    ................... 9814709.3

(51) Int. Cl.
*A61K 9/12*    (2006.01)

(52) U.S. Cl. ........................................................ 424/45
(58) Field of Classification Search .................... 424/45
See application file for complete search history.

(56) References Cited

U.S. PATENT DOCUMENTS 5,141,674 A * 8/1992 Leigh ............................. 516/1
5,876,760 A * 3/1999 Sasatani et al. ............. 424/494

FOREIGN PATENT DOCUMENTS

| WO | WO92/08446 | * | 5/1992 |
| WO | 96 19968 A | | 7/1996 |
| WO | WO96/19968 | * | 7/1996 |
| WO | WO96/41628 | * | 12/1996 |
| WO | 97 36574 A | | 10/1997 |
| WO | 98 29098 A | | 7/1998 |

* cited by examiner

*Primary Examiner*—San ming Hui
(74) *Attorney, Agent, or Firm*—Robert J. Smih

(57) ABSTRACT

The present invention relates to novel pharmaceutical aerosol formulations comprising: (A) a therapeutic agent in the form of particles coated by at least one coating excipient and at least one surfactant, in suspension in (B) a liquefied propellant gas for the administration of therapeutic agents particularly by the pulmonary route and to process for preparing these formulations. It also relates to novel particles suitable for use in such formulations.

35 Claims, No Drawings

PHARMACEUTICAL AEROSOL FORMULATION

This application is a continuation of U.S. application Ser. No. 09/673,426 filed Dec. 12, 2000 now abandoned; for which application PCT/EP99/02535 was filed internationally on Apr. 15, 1999 designating the United States; and for which priority is claimed from GB9808152.4, filed Apr. 18, 1998 and GB9814709.3, filed Jul. 8, 1998; the disclosures of which are incorporated herein by reference.

The present invention relates to novel pharmaceutical aerosol formulations for the administration of therapeutic agents particularly by the pulmonary route and to a process for preparing these formulations. It also relates to novel particles suitable for use in such formulations.

The use of aerosols for the administration of medicaments by the peripheral aerial pathways has been known for several decades. Such aerosols generally contain the therapeutic agent, one or more adjuvants such as solvents or surfactants and one or more propellants.

The most commonly used propellants in the past are chlorofluorocarbons, such as $CCl_3F$ (Freon® 11), $CCl_2F_2$ (Freon® 12) or $CF_2ClCF_2Cl$ (Freon® 114). However, the recent phasing out of these propellant gases due to their harmful effect on the ozone layer has caused manufacturers of aerosol sprays to use new propellant gases which protect stratospheric ozone.

Such "ozone-friendly" gases, also known as green gases, for example encompass hydrogen-containing chlorofluorocarbons, hydrogen-containing fluorocarbons and perfluorocarbons.

A specific group of therapeutic agents administered by the pulmonary route are antiasthmatics including bronchodilators and antiinflammatories of steroid type having a local therapeutic action in the lungs and/or a systemic therapeutic action after absorption in the blood.

For such medicaments, the replacement of the usual chlorofluorocarbon propellants by the novel propellants which protect the ozone layer can be accompanied by problems of stability of the suspensions.

This is because the change in the polarity of the propellant sometimes results in a partial solubility of the drug in the gas. This partial solubility may lead to an undesirable increase in the size of the particles during storage and/or the formation of aggregates. The valves of the administration device are then observed to block and/or the aggregates of particles penetrate less well into the fine lower respiratory pathways.

International Patent Application No. WO 92/08446 (Glaxo Group Limited) and EP-A-0 493437 (Riker Laboratories Inc) disclose the presence of surfactants in pharmaceutical aerosol formulations, however, the use of lactose or other sugars is not described. WO 94/03153 (Glaxo Group Limited) discloses a suspension formulation of beclomethasone dipropionate, but specifically excludes the presence of a surfactant. WO 93/11743, WO 93/11744 and WO 93/11745 (Glaxo Group Limited) also disclose suspension formulations of drugs which specifically exclude the presence of surfactant. WO 97/35562 (Danbiosyst) describes the process of incorporating a drug into polysaccharide microspheres by spray drying, however, the use of disaccharides, such as lactose in such a process is specifically excluded. Furthermore, there is no disclosure of their use in formulations containing a liquefied propellant gas. WO 91/16882 (Liposome Technology) discloses a process for spray drying a drug/lipid-containing ethanol solution, but there is no mention of employing a surfactant in this process. EP-A-550031 (Hoechst) discloses pressurised aerosol formulations containing spray-dried product, wherein the spray-dried product is obtained by spray-drying a solution of drug, surfactant and (optionally) auxiliary substance to give a finely dispersed matrix.

We have now discovered that it is possible to improve the stability of suspensions of drugs in the propellant by protecting the drug particles from the propellant gas with a coating. This protective layer prevents the partial solubilization of the drug in the propellant and the formation of aggregates. In combination with a surfactant, this coating excipient thus makes it possible to obtain aerosol formulations for pulmonary administration which, protected from atmospheric moisture, are stable for months and make it possible to deliver drug particles having sizes which are sufficiently small to penetrate into the respiratory pathways.

A first subject of the present invention is consequently a pharmaceutical aerosol formulation comprising a therapeutic agent in the form of coated particles in suspension in a propellant.

A further subject of the present invention is the process for preparing these particles and pharmaceutical formulations.

A still further subject are the coated drug particles.

Further subjects will become apparent to those skilled in the art from the following description and examples.

The present invention thus provides pharmaceutical aerosol formulations comprising
 (A) a therapeutic agent in the form of particles coated by at least one coating excipient and at least one surfactant, in suspension in
 (B) a liquefied propellant gas The therapeutic agents which can be used in these aerosol formulations are all solid drugs which can be administered by the pulmonary route and which are insoluble, or very slightly soluble, in the medium which is used to coat the drug particles.

A drug is regarded as insoluble or very slightly soluble if it dissolves to less than 0.1% (m/v) in the suspending medium used for the coating.

These therapeutic agents encompass in particular bronchodilators and steroidal antiinflammatories commonly used in the treatment of asthma, such as beclomethasone dipropionate, salbutamol (eg as sulphate or free base), salmeterol (eg as 1-hydroxy-2-naphthoate salt), fluticasone propionate or solvates thereof. Other compounds of interest include (2R, 3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (eg as maleate salt) and 6α,9α-Difluoro-11β-hydroxy-16α-methyl-3-oxo-17α-propionyloxy-androsta-1,4-diene-17β-carbothioic acid S-(2-oxo-tetrahydro-furan-3-yl) ester and 6α,9α-Difluoro-11β-hydroxy-16α,17α-isopropylidenedioxy-3-oxo-androsta-1, 4-diene-17β-carbothioic acid S-(2-oxo-tetrahydro-furan-3-yl) ester.

Among these, use is preferably made of beclomethasone dipropionate and in particular of its monohydrate. Use in relation to salmeterol xinafoate is also preferred.

The pharmaceutical formulations may of course also contain a combination of two or more therapeutic agents which can be administered by the pulmonary route. An example of such a combination is fluticasone propionate and salmeterol xinafoate.

The particles are coated, according to the present invention, with a protective layer comprising at least one coating excipient. This coating excipient must be physiologically acceptable when it is used in administration by the aerial pathways. In order to efficiently protect the drug particles, it must in addition be essentially insoluble in the propellant. Furthermore, the process for the preparation of the coating requires that the coating excipient be soluble in the suspending medium used to prepare the formulation, which is preferably an aqueous medium.

A beneficial coating effect can be obtained with a coating layer covering the major surface of the particles. In order to achieve optimal protection of the drug particles at least about 80% and more preferably at least about 90% of their surface should be covered by the coating layer.

The coating excipients which satisfy all these requirements are chosen from mono-, di- or polysaccharides, such as mannitol, lactose, trehalose, dextrose, microcrystalline cellulose, sodium carboxymethylcellulose, methylhydroxypropylcellulose or sorbitol.

Among these, use is preferably made of one of the two diglucosides lactose and trehalose.

The drug particles are coated not only with a coating excipient described above but also with at least one surfactant. This surfactant must be physiologically acceptable when it is used by inhalation. It must be insoluble (or essentially insoluble) in the liquefied propellant gas or gases and must not have affinity therewith. This surfactant essentially acts as a stabiliser for the slurry of drug particles in the aqueous coating medium Examples of surfactants which can be used according to the present invention are anionic surfactants such as oleic acid, non-ionic surfactants such as sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of ethylene oxide and of propylene oxide, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400 or glyceryl monolaurate, or cationic surfactants, such as cetylpyridinium chloride or benzalkonium chloride. Other examples of surfactants include synthetic phosphatides eg. distearoylphosphatidylcholine.

Use will preferably be made of lecithin.

The coating of the drug particles of the present invention can optionally comprise, in addition to the surfactant and the coating excipient, a vegetable oil chosen from olive oil, corn oil, cottonseed oil and sunflower seed oil.

The propellant which can be used according to the present invention is any liquifiable fluorocarbon, hydrogen-containing fluorocarbon or hydrogen-containing chlorofluorocarbon having a sufficient vapour pressure to enable it to act as a propellant. The propellant must be essentially non solvent for the coated drug particles, that is to say for the therapeutic agent, the coating excipient and the surfactant. Appropriate propellants include, for example, $C_{1-4}$ hydrochlorofluorocarbons, such as $CH_2ClF$, $CClF_2CHClF$, $CF_3CHClF$, $CHF_2CClF_2$, $CHClFCHF_2$, $CF_3CH_2Cl$ and $CClF_2CH_3$, $C_{1-4}$ hydrofluorocarbons, such as $CHF_2CHF_2$, $CF_3CH_2F$, $CHF_2$—$CH_3$ and $CF_3CHFCF_3$, and perfluorocarbons such as $CF_3CF_3$ and $CF_3CF_2CF_3$, or mixtures of these. Particularly preferred propellants include $CF_3CH_2F$, $CF_3CHFCF_3$ and mixtures thereof. Use is preferably made of a single propellant of hydrofluorocarbon or hydrochlorofluorocarbon type and in particular of 1,1,1,2-tetrafluoroethane ($CF_3CH_2F$) (HFA 134a).

The coated drug particles of the aerosol formulations of the present invention must have sizes which allow them to be administered by inhalation. The particles must be sufficiently small, on the one hand, to penetrate into the pulmonary pathways without encountering obstacles and, on the other hand, they must have a sufficiently large size to deposit in the lung and not to be carried away by exhalation.

The penetration of the drug particles as far as the pulmonary bronchioli and alveoli is only possible for particles having a mean size of less than 10 µm, preferably of less than 5 µm.

The size of the coated drug particles of the present invention is preferably within the range from 0.5 µm to 10 µm, in particular from 1 µm to 5 µm.

The pharmaceutic compositions according to the invention may also comprise other pharmaceutically acceptable ingredients such as solvents or surfactants. In a preferred embodiment of the present invention, the formulations contain no surfactant besides that coated on the drug particles and no co-solvents.

The present invention also provides a method for preparing a pharmaceutical aerosol formulation which consists in coating drug particles with at least one coating excipient and with at least one surfactant and in packaging them, together with the propellant, in a pressurised cartridge.

The process for the preparation of the pharmaceutical aerosol formulation of the present invention comprises, more specifically, the stages which consist (a) in preparing a suspension containing
the therapeutic agent in the form of particles,
a suspending medium which is a non-solvent for the therapeutic agent,
the coating excipient dissolved in the suspending medium and
the surfactant;

(b) in spray drying the suspension of the therapeutic agent obtained in stage (a), so as to obtain drug particles coated by the excipient and by the surfactant;

(c) suspending the coated drug particles obtained in stage (b) in the liquefied propellant gas.

The particles of therapeutic agent used in step (a) will also be of size suitable for inhalation eg of mean size less than 10 µm (eg 0.5 µm-10 µm) preferably less than 5 µm (eg 1 µm-5 µm).

In one embodiment of the process of the invention, the suspension of stage (a) above is prepared by dissolving the excipient and by dispersing the surfactant in the said suspending medium and by subsequently dispersing the drug particles in the colloidal solution thus obtained.

It is also possible, according to another embodiment of the process of the invention, to adsorb, in a first step, the surfactant on the uncoated drug particles and subsequently to disperse the particle/surfactant combination in the suspending medium containing, in the dissolved form, the coating excipient.

The suspending medium used for coating of the drug particles has to be essentially non solvent for the therapeutic agent and a good solvent for the coating excipient. The preferred suspending medium is water. The content of therapeutic agent in the suspension prepared in stage (a) can vary within wide limits. It is generally within the range from 1 to 40% (mass/volume), preferably in the range from 5 to 20% (mass/volume).

The ratio of the coating excipient to the therapeutic agent in the suspension before spray drying is between 1 and 20% by weight, preferably between 5 and 10% by weight.

The ratio of the surfactant to the therapeutic agent in the suspension obtained in stage (a) is generally between 1 and 20% by weight, preferably between 5 and 10% by weight.

The suspension described above is subsequently subjected to spray drying in an appropriate device. The suspension to be dried is dispersed as fine droplets in a stream of hot air, which instantaneously transforms them into small grains of powder. A person skilled in the art would know how to adjust the operating parameters, such as the flow rate of the suspension arriving in the drying chamber, the size of the nozzle, the inlet and outlet temperature, the atomising pressure and the flow rate of the atomising air, according to the recommendations of the manufacturer and as a function of the characteristics of the product which he desires to obtain.

A suitable spray dryer which makes possible the drying of the drug particles of the present invention is the Büchi 191 Mini Spray Dryer (Büchi Company, Switzerland). The physical parameters of the atomisation in such a device which make it possible to obtain the coated particles of active principle from the suspension of stage (a) are as follows:

Inlet air temperature: 110-170° C.
Outlet air temperature: 70-120° C.
Atomising air flow rate: 400-1000 liters per hour (preferably 400-800 liters per hour)
Pumps speed: 10-45 rpm (preferably 10-15 rpm). Typically this equates to 2-10 liters per minute (preferably around 3 ml per minute).

The spray-dried material obtained is composed of particles having a mean size of between 1 mm and 10 μm and a water content of between 0.1 and 5% by weight.

Another suitable spray dryer which makes possible the drying of the drug particles of the present invention is the NIRO Minor Mobile Spray Dryer. The physical parameters of the atomisation in such a device which make it possible to obtain the coated particles of active principle from the suspension of stage (a) are as follows:

Inlet air temperature: 100-220° C.
Outlet air temperature: 60-120° C.
Atomising airflow rate: 50-130 m$^3$/h
Suspension flow rate: 300-5000 ml/h The spray-dried material obtained is composed of particles having a mean size of between 0.1 μm and 10 μm and a water content of between 0.1 and 5% by weight.

If necessary, the particles obtained by spray drying can be subjected to micronisation or to any other method which is able to reduce their mean size to a value of less than 10 μm and preferably of less than 5 μm. Indeed, spray drying may result in partial aggregation of the particles bound to each other by the coating layer, this aggregation increasing substantially the apparent mean size of the particles.

The main purpose of this step is to break up these aggregates. It is optional and its usefulness depends, of course, on the presence of aggregates, in other words on the size of the particles after spray drying.

Micronisation is carried out in devices known as compressed-air micronisers or fluid jet mills. In these devices, the particles are carried by a strong stream of air into a chamber designed so that the particles are subjected therein to a large number of impacts. According to the invention, in order to obtain coated drug particles having an appropriate size, these devices will be made to operate at a pressure of between 8 and 14 bar, preferably between 9 and 12 bar.

The cartridges may be filled by any means which makes it possible to obtain a homogeneous suspension of the coated drug particles in the propellant. The cartridges can be filled, for example, first with the powder and then with the propellant ('dual stage') or alternatively with a prepared suspension of the powder in the propellant ('single stage').

This filling will preferably be carried out in a controlled atmosphere with a low relative humidity, in order to limit the hydration of the particles during filling.

Cartridges will generally be fitted with a metering valve and a metered dose inhaler (MDI) will comprise such a cartridge and valve together with a channelling device suitable for delivery of the formulation to the lung.

The cartridges are preferably but not necessarily stored in a packaging composed of a film which is impermeable to atmospheric moisture. The suspensions contained in these overwrapped cartridges are stable for several months at room temperature (25° C.). Other means to resist ingress of moisture to the canister may also be employed.

EXAMPLES

The following examples are intended to illustrate the invention but do not have a limiting nature.

Example 1

0.5 g of lactose and 0.5 g of lecithin are dissolved in 100 ml of demineralized water at room temperature. After obtaining a colloidal solution, 5 g of beclomethasone dipropionate monohydrate (BDP) as micronised particles are dispersed with stirring in the aqueous solution. The suspension thus obtained contains 5% BDP, 0.5% lecithin and 0.5% lactose.

This suspension is then spray-dried in a Büchi 191 Mini Spray Dryer operating with the following parameters:

Inlet air temperature: 160° C.
Outlet air temperature: 105° C.
Compressed air pressure: 9.5 bar
Atomising airflow rate: 1000 liters per hour
Pump speed: 15 rpm (typically this equates to 3 ml per minute).

The yield of the spray drying is between 60 and 70%.

The spray dried material obtained is micronised in a fluid jet mill (MCC 50, JET Pharma S.A.) under a pressure of 9 bar.

ESCA (electronic spectrometric chemical analysis) data of the micronised particles showed that at least 90% of the particle surface was covered by the coating layer after micronisation.

The characteristics of the particles before being placed in cartridges are as follows:
mean diameter: 1.5 μm (100% of the particles having a size of less than 5 μm)
water content: 0.6%

The cartridges are filled manually in a controlled atmosphere room (20±2° C., relative humidity of less than 15%) by successively introducing the micronised material and then the gas. The gas used is pressurised HFA134a gas.

The cartridges are overwrapped with a film which is impermeable to atmospheric moisture.

The finished product thus obtained is stable for several months at room temperature (25° C.).

Example 2

0.5 g of trehalose and 0.5 g of lecithin are dissolved in 100 ml of demineralized water at room temperature. After obtaining a colloidal solution, 5 g of beclomethasone dipropionate monohydrate (BDP) as micronised particles are dispersed with stirring in the aqueous solution. The suspension thus obtained contains 5% BDP, 0.5% lecithin and 0.5% trehalose.

This suspension is spray dried in a Büchi 191 Mini Spray Dryer operating with the following parameters:

Inlet air temperature: 160° C.
Outlet air temperature: 105° C.
Compressed air pressure: 9.5 bar
Atomising air flow rate: 1000 liters per hour
Pump speed: 15 rpm (typically this equates to 3 ml per minute).

The yield of the spray drying is between 60 and 70%.

The spray dried material obtained is micronised in a fluid jet mill (MCC 50, JET Pharma S.A.) under a pressure of 9 bar.

The particles, before being placed in cartridges, have a mean diameter of 1.5 μm (100% of the particles having a size of less than 5 μm).

The cartridges are filled manually in a controlled atmosphere room (20±2° C., relative humidity of less than 15%) by successively introducing the micronised material and then the gas. The gas used is pressurised HFA134a gas.

The cartridges are overwrapped with a film which is impermeable to atmospheric moisture.

Example 3

20 g of micronised particles of beclomethasone dipropionate monohydrate are triturated with 1 g of lecithin in a mortar until a homogeneous physical mixture is obtained. 2 g of lactose are dissolved in 100 ml of demineralized water at room temperature. The BDP/lecithin physical mixture is subsequently dispersed with stirring in the aqueous lactose solution. The suspension thus obtained contains 20% BDP, 1% lecithin and 2% lactose.

This suspension is spray dried in a Büchi 191 Mini Spray Dryer operating with the following parameters:

Inlet air temperature: 145° C.
Outlet air temperature: 110° C.
Compressed air pressure: 6 bar
Atomising air flow rate: 400 liters per hour
Pump speed: 15 rpm (typically this equates to 3 ml per minute).

The yield of the spray drying is approximately 10%.

The spray dried material obtained is micronised in a fluid jet mill (MCC 50, JET Pharma S.A.) under a pressure of 9 bar.

The characteristics of the particles, before being placed in cartridges, are as follows:
mean diameter: 1.5 μm (100% of the particles having a size of less than 5 μm)
water content: 0.9%

The cartridges are filled manually in a controlled atmosphere room (20±2° C., relative humidity of less than 15%) by successively introducing the micronised material and then the gas. The gas used is pressurised HFA134a gas.

The cartridges are overwrapped with a film which is impermeable to atmospheric moisture.

Example 4

2 g of lactose and 2 g of lecithin are dissolved in 100 ml of demineralized water at room temperature. After obtaining a colloidal solution, 20 g of beclomethasone dipropionate monohydrate (BDP) as micronised particles are dispersed with stirring in the aqueous solution. The suspension thus obtained contains 20% BDP, 2% lecithin and 2% lactose.

This suspension is then spray dried in a Büchi 191 Mini Spray Dryer operating with the following parameters:

Inlet air temperature: 150° C.
Outlet air temperature: 100° C.
Compressed air pressure: 6 bar
Atomising air flow rate: 400 liters per hour
Pump speed: 15 rpm (typically this equates to 3 ml per minute).

The yield of the spray drying is between 50 and 60%.

The spray dried material is micronised in a fluid jet mill (MCC 50, JET Pharma S.A.) under a pressure of 9 bar.

ESCA data of the micronised particles showed that at least 90% of the particle surface was still covered by the coating layer after micronisation.

The particles, before being placed in cartridges, have a mean diameter of 1.5 μm (100% of the particles having a size of less than 5 μm).

The cartridges are filled manually in a controlled atmosphere room (20±2° C., relative humidity of less than 15%) by successively introducing the micronised material and then the gas. The gas used is pressurised HFA134a gas.

The cartridges are overwrapped with a film which is impermeable to atmospheric moisture.

Example 5

2 g of lecithin are dissolved in 100 ml of demineralized water at room temperature. 20 g of beclomethasone dipropionate monohydrate are pre-mixed with 2 g of lactose and the blend dispersed under stirring in the lecithin aqueous solution.

The suspension is spray dried in a Büchi 191 Mini Spray Dryer with parameters as described in Example 4.

The particles, before being placed in cartridges, have a mean diameter of 1.5 μm (100% of the particles having a size of less than 5 μm).

The cartridges are filled manually in a controlled atmosphere room (20±2° C., relative humidity of less than 15%) by successively introducing the micronised material and then pressurised HFA134a gas.

The cartridges are overwrapped with a film which is impermeable to atmospheric moisture.

Cartridges were prepared with composition on analysis as follows:

For a 250 μg/dose product (63 μl metering valve):

| | |
|---|---|
| BDP: | 40 mg |
| Lecithin: | 4 mg |
| Lactose | 4 mg |
| HFA134a | 11.952 g |

For a 100 μg/dose product (63 μl metering valve):

| | |
|---|---|
| BDP: | 16 mg |
| Lecithin: | 1.6 mg |
| Lactose | 1.6 mg |
| HFA134a | 11.981 g |

For a 50 μg/dose product (63 μl metering valve):

| | |
|---|---|
| BDP: | 8 mg |
| Lecithin: | 0.8 mg |
| Lactose | 0.8 mg |
| HFA134a | 11.990 g |

Example 6

15 g of lecithin are dissolved in 1000 ml of demineralized water at room temperature (20° C.±2° C.). 150 g of beclomethasone dipropionate monohydrate are pre-mixed with 15 g of lactose and the blend dispersed under stirring in the lecithin aqueous solution.

The suspension is spray dried in a NIRO Minor Mobile spray dryer using the following parameters:

Inlet air temperature: 160° C.
Outlet air temperature: 93° C.
Compressed air pressure (rotary atomiser): 6 bars (32 000 rpm)
Atomising air flow rate: 100 m³/h
Pump speed: 353 ml per hour The yield of the spray drying is between 50 and 90%. The water content of the powder is between 0.5 and 1% (m/m).

The particles prior to micronisation have a mean diameter of 23.6 μm.

The spray dried material is micronised in a fluid jet mill (MCC 50, JET Pharma S.A.).

The particles before being placed in cartridges, have a mean diameter of 1.5 μm (100% of the particles having a size of less than 5 μm).

The cartridges are filled automatically in a controlled atmosphere room (20° C.+−2° C., relative humidity of less than 15%) by using a filling machine such as a Pamasol system. The micronised material is successively introduced and mixed with HFA 134a and then pressurised HFA134a gas only is used to clean cartridge valves.

The cartridges are overwrapped with a film which is impermeable to atmospheric moisture.

Cartridges are overwrapped and composition analysis gave the following results:

For a 250 μg/dose product (63 μl metering valve):

| | |
|---|---|
| BDP: | 40 mg |
| Lecithin: | 4 mg |
| Lactose: | 4 mg |
| HFA134a: | 11.952 g |

For a 100 μg/dose product (63 μl metering valve):

| | |
|---|---|
| BDP: | 16 mg |
| Lecithin: | 1.6 mg |
| Lactose: | 1.6 mg |
| HFA134a: | 11.981 g |

For a 50 μg/dose product (63 μl metering valve):

| | |
|---|---|
| BDP: | 8 mg |
| Lecithin: | 0.8 mg |
| Lactose: | 0.8 mg |
| HFA134a: | 11.990 g |

Example 7

22.5 g of lecithin are dissolved in 1500 ml of demineralized water at room temperature (20° C.±2° C.). 225 g of beclomethasone dipropionate monohydrate are pre-mixed with 22.5 g of lactose and the blend is dispersed under stirring in the lecithin aqueous solution.

The suspension is spray dried in a NIRO Minor Mobile spray dryer using the following parameters:

Inlet air temperature: 160° C.
Outlet air temperature: 87-90 ° C.
Compressed air pressure (rotary atomiser): 6.5 bars
Atomising air flow rate: 100 m³/h
Pump speed: 353 ml per hour The yield of the spray drying is between 50 and 90%. The water content of the powder is between 0.5 and 1% (m/m).

The particles prior to micronisation have a mean diameter of 19 μm.

Example 8

22.5 g of lecithin are dissolved in 1500 ml of demineralized water at room temperature (20° C. ±2° C.). 225 g of beclomethasone dipropionate monohydrate are pre-mixed with 22.5 g of lactose and the blend is dispersed under stirring in the lecithin aqueous solution.

The suspension is spray dried in a NIRO Minor Mobile spray dryer using the following parameters:

Inlet air temperature: 160° C.
Outlet air temperature: 91-92° C.
Compressed air pressure (rotary atomiser): 6.5 bars
Atomising air flow rate: 100 m³/h
Pump speed: 353 ml per hour The yield of the spray drying is between 50 and 90%. The water content of the powder is between 0.5 and 1% (m/m).

The particles prior to micronisation have a mean diameter of 25.3 μm.

The spray-dried material is micronised in a fluid jet mill (MCC 50, JET Pharma S.A.).

The particles before being placed in cartridges, have a mean diameter of 1.5 μm (100% of the particles having a size of less than 5 μm).

Example 9

30 g of lecithin are dissolved in 2000 ml of demineralized water at room temperature (20° C.±2° C.). 300 g of beclomethasone dipropionate monohydrate are pre-mixed with 30 g of lactose and the blend dispersed under stirring in the lecithin aqueous solution.

The suspension is spray dried in a NIRO Minor Mobile spray dryer using the following parameters:

Inlet air temperature: 160° C.
Outlet air temperature: 93-94° C.
Compressed air pressure (rotary atomiser): 6.5 bars
Atomising air flow rate: 100 m³/h
Pump speed: 480 ml per hour The yield of the spray drying was between 50 and 90%. The water content of the powder is between 0.4 and 1% (m/m).

The particles prior to micronisation have a mean diameter of 21.4 μm.

The spray-dried material is micronised in a fluid jet mill (MCC 50, JET Pharma S.A.).

The particles before being placed in cartridges, have a mean diameter of 1.7 μm (100% of the particles having a size of less than 5 μm).

The cartridges are filled automatically in a controlled atmosphere room (20° C.±2° C., relative humidity of less than 15%) by using a filling machine such as a Pamasol system. The micronised material is successively introduced and mixed with HFA 134a and then pressurised HFA134a gas only is used to clean cartridges valves.

The cartridges are overwrapped with a film which was impermeable to atmospheric moisture.

Cartridges are overwrapped and composition analysis gave the following results:

For a 250 μg/dose product (63 μl metering valve):

| | |
|---|---|
| BDP: | 40 mg |
| Lecithin: | 4 mg |
| Lactose: | 4 mg |
| HFA134a: | 11.952 g |

For a 100 μg/dose product (63 μl metering valve):

| | |
|---|---|
| BDP: | 16 mg |
| Lecithin: | 1.6 mg |
| Lactose: | 1.6 mg |
| HFA134a: | 11.981 g |

For a 50 μg/dose product (63 μl metering valve):

| | |
|---|---|
| BDP: | 8 mg |
| Lecithin: | 0.8 mg |
| Lactose: | 0.8 mg |
| HFA134a: | 11.990 g |

Example 10

30 g of lecithin are dissolved in 2000 ml of demineralized water at room temperature (20° C.±2° C.). 300 g of beclomethasone dipropionate monohydrate are pre-mixed with 30 g of lactose and the blend dispersed under stirring in the lecithin aqueous solution.

The suspension is spray dried in a NIRO Minor Mobile spray dryer using the following parameters:

| |
|---|
| Inlet air temperature: 160° C. |
| Outlet air temperature: 88-94° C. |
| Compressed air pressure (rotary atomiser): 6.5 bars |
| Atomising air flow rate: 100 m³/h |
| Pump speed: 480 ml per hour |

The yield of the spray drying is between 80 and 90%. The particles prior to micronisation have a mean diameter of 12.5 μm.

The spray-dried material is micronised in a fluid jet mill (MCC 50, JET Pharma S.A.).

The particles before being placed in cartridges, have a mean diameter of 1.5 μm (100% of the particles having a size of less than 5 μm).

Example 11

15 g of lecithin are dissolved in 1000 ml of demineralized water at room temperature (20° C.±2° C.). 150 g of beclomethasone dipropionate monohydrate are pre-mixed with 15 g of lactose and the blend dispersed under stirring in the lecithin aqueous solution.

The suspension is spray dried in a NIRO Minor Mobile spray dryer using the following parameters:

| |
|---|
| Inlet air temperature: 200° C. |
| Outlet air temperature: 88-94° C. |
| Compressed air pressure (two fluid nozzle atomiser): 4 bars |
| Atomising air flow rate: 100 m³/h |
| Pump speed: 480 ml per hour |

The yield of the spray drying is between 50 and 90%.

The spray-dried material is micronised in a fluid jet mill (MCC 50, JET Pharma S.A.).

The particles before being placed in cartridges, have a mean diameter of 1.5 μm (100% of the particles having a size of less than 5 μm).

The cartridges are filled manually in a controlled atmosphere room (20° C.±2° C., relative humidity of less than 15%) by successively introducing the micronised material and then pressurised HFA134a gas.

The cartridges are overwrapped with a film which was impermeable to atmospheric moisture.

Cartridges are overwrapped and composition analysis gave the following results:

For a 250 μg/dose product (63 μl metering valve):

| | |
|---|---|
| BDP: | 40 mg |
| Lecithin: | 4 mg |
| Lactose: | 4 mg |
| HFA134a: | 11.952 g |

Example 12

30 g of lecithin are dissolved in 2000 ml of demineralized water at room temperature (20° C.±2° C.). 150 g of beclomethasone dipropionate monohydrate are pre-mixed with 30 g of lactose and the blend dispersed under stirring in the lecithin aqueous solution.

The suspension is spray dried in a NIRO Minor Mobile spray dryer using the following parameters:

| |
|---|
| Inlet air temperature: 150° C. |
| Outlet air temperature: 83-90° C. |
| Compressed air pressure (two fluid nozzle atomiser): 6 bars |
| Atomising air flow rate: 100 m³/h |
| Pump speed: 1.41 kg/h |

The yield of the spray drying is between 50 and 90%.

The spray-dried material is micronised in a fluid jet mill (MCC 50, JET Pharma S.A.).

The particles before being placed in cartridges, have a mean diameter of 1.5 μm (100% of the particles having a size of less than 5 μm).

The cartridges are filled manually in a controlled atmosphere room (20° C.±2° C., relative humidity of less than 15%) by successively introducing the micronised material and then pressurised HFA134a gas.

The cartridges are overwrapped with a film which is impermeable to atmospheric moisture.

Cartridges are overwrapped and composition analysis gave the following results:

For a 250 µg/dose product (63 µl metering valve):

| | |
|---|---|
| BDP: | 40 mg |
| Lecithin: | 4 mg |
| Lactose: | 4 mg |
| HFA134a: | 11.952 g |

Example 13

30 g of lecithin are dissolved in 2000 ml of demineralized water at room temperature (20° C.±2° C.). 300 g of beclomethasone dipropionate monohydrate are pre-mixed with 30 g of lactose and the blend dispersed under stirring in the lecithin aqueous solution.

The suspension is spray dried in a NIRO Minor Mobile spray dryer using the following parameters:

| |
|---|
| Inlet air temperature: 170° C. |
| Outlet air temperature: 83-90° C. |
| Compressed air pressure (two fluid nozzle atomiser): 6 bars |
| Atomising air flow rate: 100 m³/h |
| Pump speed: 2.33 kg/h |

The yield of the spray drying is between 50 and 90%.

The spray-dried material is micronised in a fluid jet mill (MCC 50, JET Pharma S.A.).

The particles before being placed in cartridges, have a mean diameter of 1.5 µm (100% of the particles having a size of less than 5 µm).

The cartridges are filled manually in a controlled atmosphere room (20° C.±2° C., relative humidity of less than 15%) by successively introducing the micronised material and then pressurised HFA134a gas.

The cartridges are overwrapped with a film which is impermeable to atmospheric moisture.

Cartridges are overwrapped and composition analysis gave the following results:

For a 250 µg/dose product (63 µl metering valve):

| | |
|---|---|
| BDP: | 40 mg |
| Lecithin: | 4 mg |
| Lactose: | 4 mg |
| HFA134a: | 11.952 g |

Example 14

2 g of lecithin may be dissolved in 200 ml of demineralized water at room temperature (20° C.±2° C.). 10 g of salmeterol xinafoate as micronized particles are pre-mixed with 2 g of lactose and the blend dispersed under stirring in the lecithin aqueous solution. The suspension thus obtained contains 5% salmeterol xinafoate, 1% lecithin and 1% lactose.

The suspension may then be spray dried in a Büchi 191 Mini Spray Dryer with the following parameters:

| |
|---|
| Inlet air Temperature: 105° C. |
| Outlet air Temperature: 58° C. |
| Compressed air pressure: 7 bars |
| Atomising air flow rate: 800 Nl/h |
| Drying air flow: 28 m³/h |
| Feed flow: 5 ml/h |

The yield of the spray drying should be around 70%. The water content of powder should be less than 0.5% (m/m).

The particles before being micronized should have a mean diameter between 2 and 5 µm.

The spray dried material obtained may be micronized in a fluid jet mill (MC 50, JET Pharma S.A.) under a pressure of 8 bars.

The particles before being placed in cartridges should have a mean diameter around 1.5 µm The cartridges may be filled manually by successively introducing the micronized material and then pressurised HFA 134a gas.

The invention claimed is:

1. A pharmaceutical aerosol formulation comprising:
therapeutic drug particles having a first spray-dry coating of at least one excipient selected from the group consisting of lactose and trehalose and a second spray-dry coating of at least one surfactant, said coated therapeutic drug particles being in suspension in a liquid propellant selected from the group consisting of 1,1,1,2-tetrafluoroethane, 1,1,1,2,3,3,3-heptafluoropropane and mixtures thereof.

2. The pharmaceutical aerosol formulation of claim 1, wherein said therapeutic drug particles are suitable for being administered by the pulmonary route, and wherein said therapeutic drug particles are insoluble in said suspending medium.

3. The pharmaceutical aerosol formulation of claim 2, wherein said therapeutic drug particles are selected from the group consisting of beclomethasone, salbutamol, salmeterol, fluticasone, suitable salts, esters and solvates thereof, and combinations thereof.

4. The pharmaceutical aerosol formulation of claim 1, wherein said therapeutic drug particles are selected from the group consisting of beclomethasone dipropionate, beclomethasone dipropionate monohydrate, fluticasone propionate, salbutamol sulphate, salmeterol xinafoate and combinations thereof.

5. The pharmaceutical aerosol formulation of claim 4, wherein said therapeutic drug particles comprise a combination of salmeterol xinafoate and fluticasone propionate.

6. The pharmaceutical aerosol formulation of claim 1, wherein said surfactant is suitable for being administered by the pulmonary.

7. The pharmaceutical aerosol formulation of claim 6, wherein said surfactant is selected from the group consisting of oleic acid, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of ethylene oxide and of propylene oxide, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, glyceryl monolaurate, cetylpyridinium chloride and benzalkonium chloride.

8. The pharmaceutical aerosol formulation of claim 7, wherein said surfactant comprises lecithin.

9. The pharmaceutical aerosol formulation of claim 1, wherein said therapeutic drug particles include a third coating, said third coating comprising a vegetable oil.

10. The pharmaceutical aerosol formulation of claim 9, wherein said vegetable oil is selected from the group consisting of olive oil, corn oil, cottonseed oil and sunflower seed oil.

11. The pharmaceutical aerosol formulation of claim 1, wherein said propellant comprises 1,1,1,2-tetrafluoroethane.

12. The pharmaceutical aerosol formulation of claim 1, wherein said therapeutic drug particles have a mean size in the range of approximately 0.5 to 10 μm.

13. The pharmaceutical aerosol formulation of claim 12, wherein said therapeutic drug particles have a mean size in the range of approximately 1 to 5 μm.

14. The pharmaceutical aerosol formulation of claim 1, wherein said aerosol formulation further includes at least one solvent.

15. A process for preparing a pharmaceutical aerosol formulation, comprising the steps of:

providing a therapeutic agent, said therapeutic agent being in the form of particles;

providing a suspending medium, said therapeutic agent particles being insoluable in said suspending medium;

preparing a suspension by placing said therapeutic agent particles and at least one surfactant in said suspending medium, said suspension preparation step further including the step of dissolving at least one excipient in said suspending medium;

spray drying said suspension to obtain therapeutic agent particles coated with said excipient and said surfactant; and suspending said coated therapeutic agent particles in a propellant gas.

16. The process of claim 15, wherein said process includes the step of reducing the size of said coated therapeutic agent particles prior to said step of suspending said coated therapeutic agent particles in said propellant gas.

17. The process of claim 15, wherein the mean size of said coated therapeutic agent particles is in the range of approximately 0.5 to 10 μm.

18. The process of claim 17, wherein said mean size of said coated therapeutic agent particles is in the range of approximately 1 μm to 5 μm.

19. The process of claim 15, wherein said suspending medium comprises a medium that is a solvent for said excipient.

20. The process of claim 19, wherein said suspending medium comprises water.

21. The process of claim 15, wherein said suspending step comprises suspending directly said therapeutic agent particles in said suspending medium containing said dissolved excipient and said surfactant.

22. The process of claim 15, wherein said suspending step comprises two successive steps comprising (i) re-absorbing said surfactant onto said therapeutic agent particles to form second therapeutic agent particles, and (ii) suspending said second therapeutic agent particles in said suspending medium containing said excipient, in dissolved form.

23. The process of claim 15, wherein the content of said therapeutic agent particles in said suspension is in the range of approximately 1 to 40% (mass/volume).

24. The process of claim 23, wherein said content of said therapeutic agent particles in said suspension is in the range of approximately 5 to 20% (mass/volume).

25. The process of claim 15, wherein the surfactant/therapeutic agent ratio in said suspension is in the range of approximately 1 to 20% by weight.

26. The process of claim 25, wherein said surfactant/therapeutic agent is in the range of approximately 5 to 10% by weight.

27. The process of claim 15, wherein the excipient/therapeutic agent ratio in said suspension is in the range of approximately 1 to 20% by weight.

28. The process of claim 27, wherein said excipient/therapeutic agent ratio is in the range of approximately 5 to 10% by weight.

29. The process of claim 15, wherein said process includes the step of filing cartridges successively with said coated therapeutic agent and subsequently with said propellant gas.

30. The process of claim 15, wherein said process includes the step of filing said cartridges with said coated therapeutic agent particles and said propellant gas in a single step.

31. The pharmaceutical aerosol formulation of claim 6, wherein said surfactant comprises a non-ionic surfactant.

32. The pharmaceutical aerosol formulation of claim 6, wherein said surfactant comprises an anionic surfactant.

33. The pharmaceutical aerosol formulation of claim 6, wherein said surfactant comprises cationic surfactant.

34. The pharmaceutical aerosol formulation of claim 1, wherein the excipient/drug ratio in said suspension is in the range of approximately 1 to 20% by weight.

35. The pharmaceutical aerosol formulation of claim 34, wherein said excipient/drug ratio is in the range of approximately 5 to 10% by weight.

* * * * *